United States Patent
Tanghoej

(10) Patent No.: US 8,230,993 B2
(45) Date of Patent: *Jul. 31, 2012

(54) CONTAINER FOR MEDICAL DEVICES

(75) Inventor: Allan Tanghoej, Kokkedal (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/820,151

(22) Filed: Jun. 22, 2010

(65) Prior Publication Data

US 2010/0252469 A1  Oct. 7, 2010

Related U.S. Application Data

(63) Continuation of application No. 12/087,861, filed as application No. PCT/DK2007/000027 on Jan. 22, 2007, now Pat. No. 7,766,163.

(30) Foreign Application Priority Data

Jan. 20, 2006 (DK) .......................... PA 2006 00090
Apr. 24, 2006 (DK) .......................... PA 2006 00569

(51) Int. Cl.
*B65D 83/10* (2006.01)

(52) U.S. Cl. ....................................... 206/364; 206/210

(58) Field of Classification Search .................. 206/205, 206/210, 363, 364, 365, 368; 604/171, 172, 604/263, 265
See application file for complete search history.

(56) References Cited

U.S. PATENT DOCUMENTS

| | | | | |
|---|---|---|---|---|
| 3,073,307 A * | 1/1963 | Stevens | .......................... | 206/365 |
| 3,149,717 A * | 9/1964 | Castelli | .......................... | 206/365 |
| 3,333,682 A * | 8/1967 | Burke | .......................... | 206/365 |
| 4,530,697 A * | 7/1985 | Kuhlemann et al. | .......... | 604/263 |
| 5,217,114 A * | 6/1993 | Gadberry et al. | ............. | 206/364 |
| 5,290,265 A * | 3/1994 | Davis et al. | ................... | 206/365 |
| 5,819,921 A * | 10/1998 | Schmid | .......................... | 206/210 |
| 6,059,107 A * | 5/2000 | Nosted et al. | ................. | 206/364 |
| 6,186,325 B1 * | 2/2001 | Schmidt et al. | ............... | 206/364 |

(Continued)

FOREIGN PATENT DOCUMENTS

JP   2001-130634   5/2001

(Continued)

OTHER PUBLICATIONS

Opposition from Astra Tech AB in corresponding EP application No. 07700165.9 and patent No. 1979032, dated Oct. 5, 2010.

(Continued)

*Primary Examiner* — Luan K Bui
(74) *Attorney, Agent, or Firm* — Coloplast Corp., Coloplast A/S; Daniel G. Chapik; Nicholas R. Baumann

(57) ABSTRACT

The present invention relates to a package comprising a container defining a compartment for containing a liquid and at least partly a medical device. The compartment extends in a longitudinal direction from a bottom of the container towards an opening of the container, wherein a first section of the compartment has a cross-sectional area which is smaller than a cross-sectional area of a second section of the compartment, and where the first section is arranged between the opening and the second section. As the cross-sectional area of the first section is smaller than the cross-sectional area of the second section the first section will function as a stop for the liquid in case the container is placed in a horizontal orientation.

11 Claims, 5 Drawing Sheets

U.S. PATENT DOCUMENTS

Figure 1:
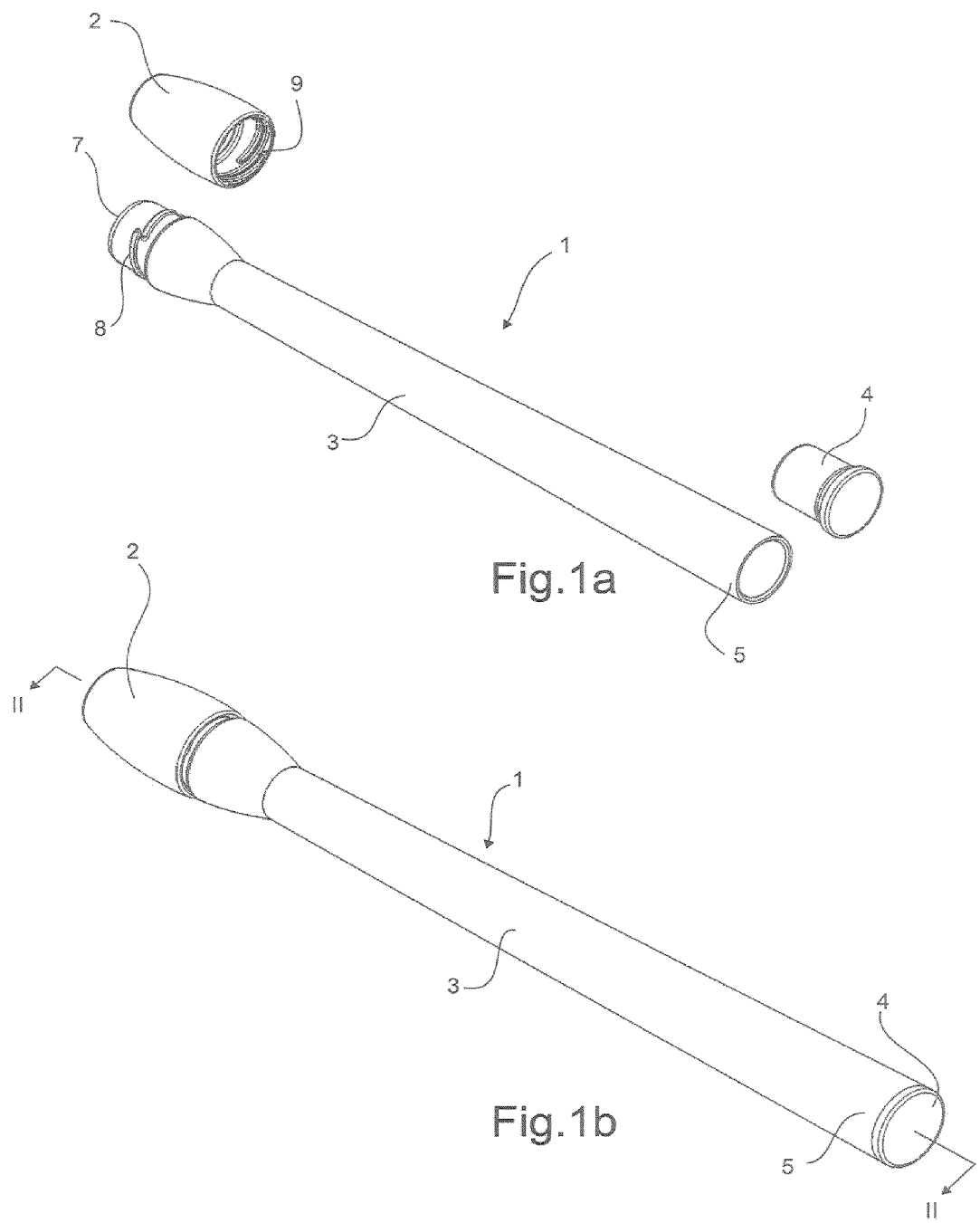

| | | | |
|---|---|---|---|
| 6,315,113 B1 * | 11/2001 | Britton et al. | 206/210 |
| 6,848,574 B1 * | 2/2005 | Israelsson et al. | 206/210 |
| 2004/0256264 A1 | 12/2004 | Israelsson et al. | |

FOREIGN PATENT DOCUMENTS

| | | |
|---|---|---|
| JP | 2005-523779 | 8/2005 |
| WO | 9321984 | 11/1993 |
| WO | 9741811 | 11/1997 |
| WO | 9811932 | 3/1998 |
| WO | 9819729 | 5/1998 |
| WO | 9930761 | 6/1999 |
| WO | 03002177 | 1/2003 |
| WO | 03002178 | 1/2003 |
| WO | 03002179 | 1/2003 |
| WO | 03008028 | 1/2003 |
| WO | 03/092779 | 11/2003 |
| WO | 2004089454 | 10/2004 |
| WO | 2005014055 | 2/2005 |

OTHER PUBLICATIONS

Opposition from Hollister Incorporated in corresponding EP application No. 07700165.9 and patent No. 1979032, dated Oct. 6, 2010.

* cited by examiner

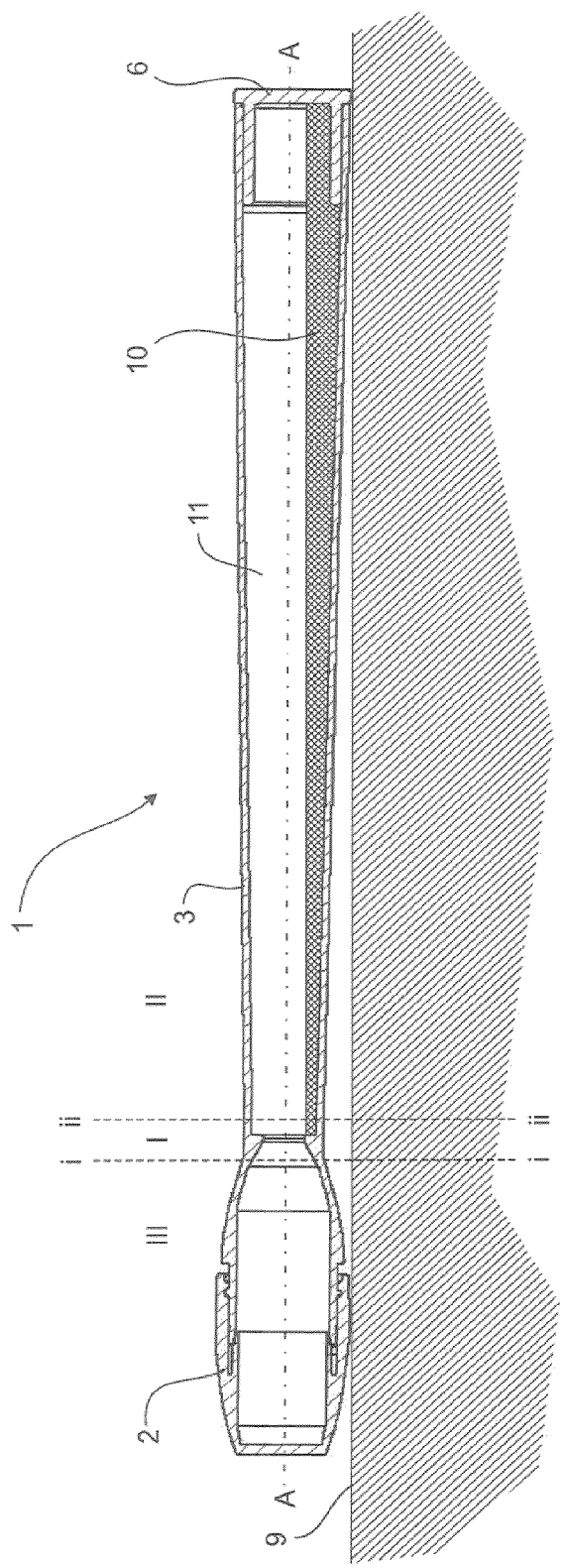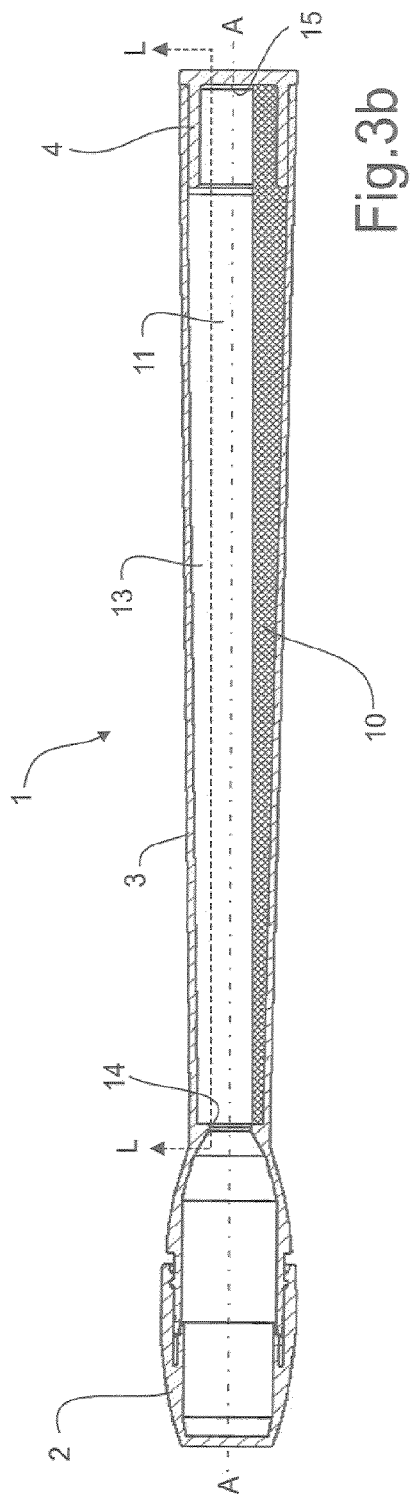

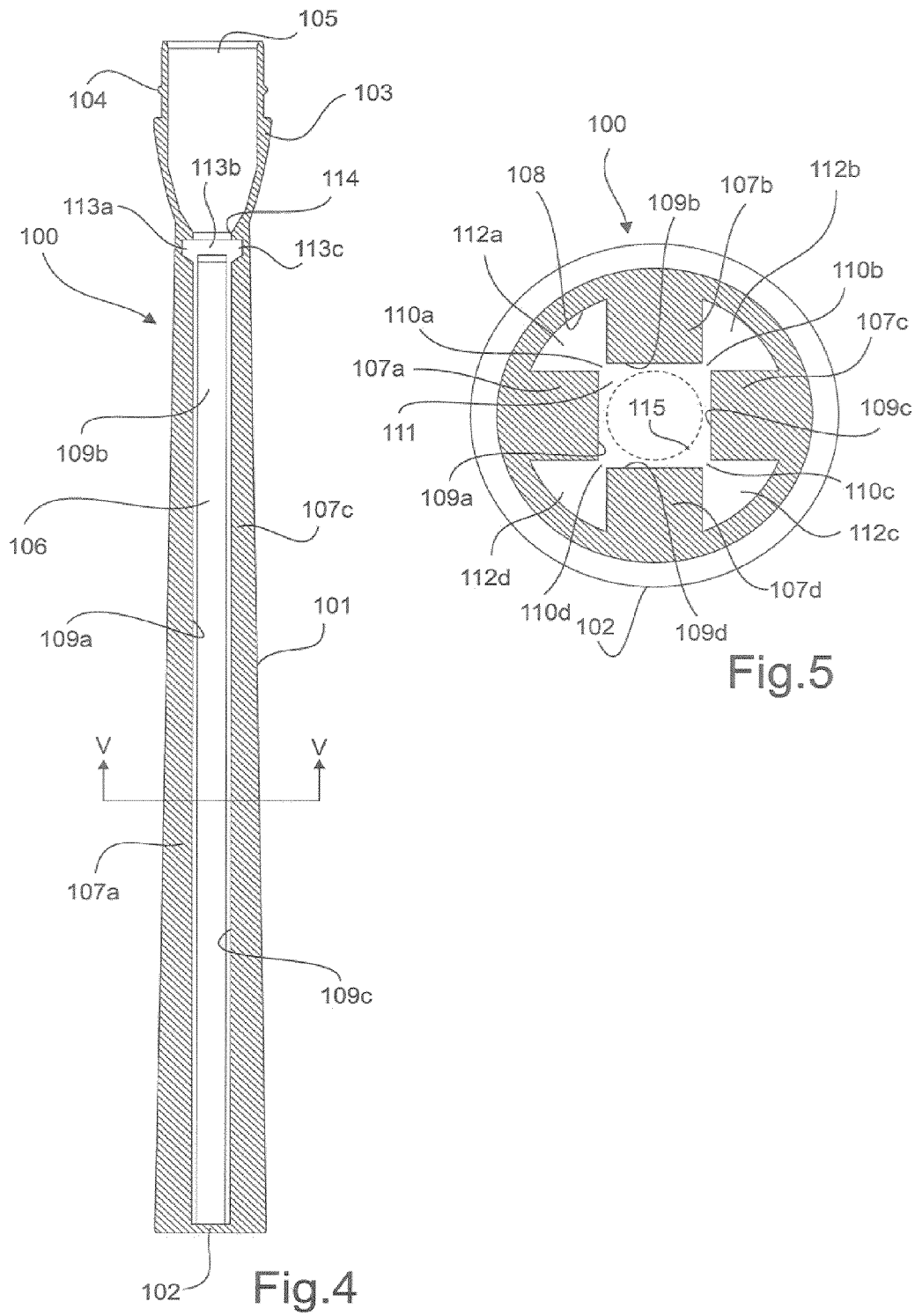

CONTAINER FOR MEDICAL DEVICES

This application is a continuation of U.S. patent application Ser. No. 12/087,861 filed Jul. 16, 2008, now U.S. Pat. No. 7,766,163, which is a 35 U.S.C. §371 national stage entry of international appln. PCT/DK2007/000027 filed on Jan. 22, 2007, which claims the benefit of foreign priority under 35 U.S.C. §119(b) to Denmark Pat. Appln. PA 2006 00090 filed on Jan. 20, 2006 and Denmark Pat. Apple. PA 2006 00569 filed on Apr. 24, 2006.

FIELD OF THE INVENTION

The present invention relates to a container for storing a medical device and a liquid, such as a pre-wetted catheter.

BACKGROUND

Containers for storing medical devices in liquids are generally known, and together the container, medical device and liquid forms a package which may be stored by e.g. pharmacies and handled by users of the medical device.

Such packages may for example be one-day disposable contact lenses, where the container generally is cylindrically shaped having a foil lid and the contact lens is soaked in a saline solution.

Other packages may for example be the SpeediCath® produced by Coloplast A/S. The SpeediCath® package comprises a foil container, consisting of two sheets of foil welded along the edges thereby forming a closed pocket wherein a coated catheter may be stored in a liquid. When used the foil package is open and the pre-wetted catheter is ready for use.

However when opening containers containing a medical device and a liquid, such as a liquid for wetting a coated catheter, the liquid will often spill out either when opening, removing the medical device or in case the containers tilts. Especially elongated containers for storing elongated medical devices, such as catheters, may easily spill out some of the liquid therefrom if the container is moved into a horizontal position, especially when the opening of the container is arranged at one of the ends of the elongated container.

By horizontal position it should be understood that the longitudinal direction of the container, i.e. the direction from the bottom to the opening, is horizontally orientated or almost horizontally orientated. In contrast thereto it should be understood that the containers vertical position is when the longitudinal direction of the container is aligned in a generally vertical direction.

SUMMARY

In a first aspect of the invention the package comprises a container defining a compartment for containing a liquid and at least partly a medical device, said compartment extending in a longitudinal direction from a bottom of the container towards an opening of the container, wherein a first section of the compartment has a cross-sectional area which is smaller than a cross-sectional area of a second section of the compartment, and where the first section is arranged between the opening and the second section.

As the cross-sectional area of the first section is smaller than the cross-sectional area of the second section the first section will function as a stop for the liquid in case the container is placed in a horizontal orientation.

Additionally, in one embodiment according to the invention a sub-compartment of the compartment may be provided. The sub-compartment is defined by a plane tangential to the smallest circumference of the first section of the compartment, and parallel to the longitudinal axis of the compartment; and the second section of the compartment. The sub-compartment forms a volume, which is larger than the volume of the liquid contained in the compartment.

This advantageously provides a sub-compartment wherein liquid will not be spilled should the container tilt or fall over in a horizontal position while being open.

It should be understood that the compartment should be adapted to contain a liquid. Thus, it should not only be properly sealed to be capable of containing e.g. a swelling liquid for catheters, but it should also be liquid tight in such a way that it may enable sustained moist environment and prevent leaks from the compartment during storage prior to use.

In one embodiment the package according to the invention may be used to hold an elongate medical device, such as a coated catheter. Thus a package, wherein the container has an elongate shape and has a dimension which is larger in the longitudinal direction than the diametrical dimension of any cross-sectional area of the container may advantageously be provided. It should be understood that the cross-section not necessarily is a circle, but the diametrical dimension also may be determined for an oval, square or other geometrical or random cross-section.

In another embodiment of the package according to the invention the container is formed with a third section of the compartment, which has a cross-sectional area which is larger than the cross-sectional area of the first section, and wherein the third section is arranged between the opening and the first section. This advantageously improves the first sections function as a liquid stop when the container is placed on a leveled surface, which is generally horizontally aligned such as the rim of a sink.

In order to prevent the catheter from accidentally slipping completely into the second section of the compartment the catheter may comprise a distal end and a proximal end, where a connector is attached to the distal end of the catheter, and wherein the outer circumference of at least a part of said connector is larger than the circumference of at least a part of the first section of the compartment.

Furthermore, the connector may be formed so that, when placed in the compartment of the container, it projects beyond the opening of the container. This allows a user to easily grab hold of the catheter and pull it out of the container.

In some types of packages the medical device may be formed of a flexible material, which may undesirably bend when the medical device is placed in or packed or otherwise stored in the container. In order to prevent such bending, for example kinking of catheters, the container can be provided with at least one support member extending in a radial direction from the inner surface of the container towards a support surface of the respective support member which is arranged in at least a part of the second section of the compartment. Furthermore, such an extending support member would also support the container itself, reducing the risk that it is unintentionally bend.

It should be understood that when the at least one support member is 'arranged in at least a part of the second section of the compartment' that the at least one support member not necessarily has to extend fully in the longitudinal direction in order to function as intended. Thus in some embodiments it may for example extend halfway from the first section into the second section of the compartment or a multiple of support members may be arranged in longitudinal alignment within the second section.

It should furthermore be understood that one or two support members may be provided in order to provide some support to the medical device. However, in one advantageous embodiment at least three support members which extend radially from the inner surface of the container towards respective support surfaces and where the respective support surfaces and a periphery distance between each neighboring support surface defines a lumen extending in the longitudinal direction (where the periphery distance is the shortest distance between each of the respective pairs of neighboring support surfaces) may be provided for improved support and guidance of the medical device. Furthermore, this provides a lumen wherein the medical device may be supported on the side while a considerable amount of liquid still may be stored in the compartment between the support members.

In one type of a package according to the invention the medical device is a telescopic catheter comprising a proximal section and a distal section, both sections forming a part of a conduit and where the two sections are capable of being arranged in a collapsed configuration and an expanded configuration where the extent of the conduit in the collapsed configuration is smaller than the extent of the conduit in the expanded configuration. Thus the telescopic catheter may be placed in the lumen when it is in its expanded configuration and pressed into its collapsed configuration where the support members will prevent that the catheter bends or kinks out to side but rather guides the catheter in its telescopic movement towards the collapsed configuration.

It is commonly understood that when referring to proximal and distal orientation of medical devices the term 'proximal' is closest to the body or furthest inserted into the body. Thus the proximal section of a telescopic catheter is the part of the catheter which is adapted to be fully inserted into the urethra or other canal of the body when the catheter is used, while the distal section of the catheter usually is adapted to at least partly be arranged outside the canal, or at least be the section closest to the exit of the canal when the catheter is in use.

This provides for a package with an expandable catheter, which can be easily collapsed after use in a controlled fashion as it will collapse into its collapsed configuration in the container wherein it conveniently can be contained until disposal. In this embodiment, it is desirable that the force which is required to collapse the catheter is higher than the force required to insert the catheter into the urethra. I.e. the coupling is sufficiently strong to maintain the expanded configuration during the bending of the catheter as it is entered through the curved passage of the urethra, in particular of male users or the passage through prostate or the sphincter. After use, when the catheter is removed from the urethra, the coupling should, on the other hand, allow collapsing of the catheter by pushing the two sections into one another, and the movement towards the collapsed configuration should preferably take place prior to kinking of the catheter.

It should thus be understood that in order to prevent bending or kinking a first longitudinal directed force required for moving the catheter from the expanded configuration to the collapsed configuration should be smaller than a second longitudinal directed force required for at least one of the proximal section and the distal section to bend.

The push-in force required to insert the catheter into the urethra has shown to be approximately 1-2N, varying from person to person. Furthermore, for catheters for insertion into the male urethra and which are formed of materials such as PVC and PU, the second longitudinal directed force is typically around 2N. Thus it can be understood that since it is undesirable that the telescopic catheter collapses when inserted into the urethra the telescopic catheter should be dimensioned so that the first longitudinal directed force is above 2N, preferably considerably above that value, for example above two times the first longitudinal directed force. However, since the second longitudinal directed force, i.e. the kinking force, is close to and in some cases maybe even identical to the push-in force the catheter would need to be very precisely dimensioned and accurately pushed into the container in order for it to be moved from the expanded configuration to the collapsed configuration without bending or kinking.

Thus, by advantageously providing support members in the container as described herein which prevents the catheter to bend or kink the second longitudinal force is in theory infinite and the telescopic catheter may thus easily be telescopically collapsed into the collapsed configuration when inserted into the container.

In order to prevent that the telescopic catheter bends out into the openings between the support members, the largest of the periphery distances is advantageously smaller than the diameter of the proximal section of the telescopic catheter.

In one embodiment the support surfaces are curved when seen in cross-section. The curve of the support surface corresponding to the curvature of the catheter. Thus, when the support surface are shaped to follow the shape of the medical device the medical device is easier inserted into the container as the support surfaces easier guides the medical device in the lumen.

In yet another embodiment of the package according to the invention the thickest width of the cross-sectional area of the second section is at least two times the thickest width of the cross-sectional area of the elongated medical device. This allows room in the container to allow the elongated medical device to be folded.

This is especially advantageous when the elongated medical device is a catheter, since such catheter typically are of a flexible material such as PVC or PU and thus is capable of folding when inserted into the container. This allows for catheters which have a longer longitudinal extend than the longitudinal extend of the container to be disposed in the container as they will curl into the container when pressed. Especially a telescopic catheter which is locked in an expanded configuration when used may be stored until disposal after use in the same container in which it was stored in its collapsed configuration prior to its use. By locked it shall be understood that the connection between the proximal section and the distal section of the telescopic catheter is so rigid in the expanded configuration that any attempt to telescopically collapse the catheter back to its collapsed configuration is practically impossible or in other words the force required to telescopically collapse the catheter is at least higher than the second longitudinal directed force whereby the catheter will kink or bend before it collapses telescopically.

Furthermore, as a used catheter is curled into the container it will be deformed whereby it is rendered useless and thus it is prevented that the catheter is reused as this would be unhygienic and greatly increase the risk of infections or diseases.

Typically catheters used in a package according to the invention are provided with a connector on their distal end, i.e. the end of the catheter which is not inserted into the urinary or other canal of the human body. Such a connector may be adapted to be coupled to external devices for example urinary bags. Furthermore the connector may also serve as a grip, which is held between the fingers when inserting the catheter. This prevents that the insertable part of the catheter is touched reducing the risk of contamination and subsequent infection of the canal wherein the catheter is inserted.

In yet another embodiment of the package according to the invention the outer circumference of the connector is larger than the circumference of the first section of the compartment. Thus the connector may not accidentally be inserted all the way into the second section when packed as the first section will function as a stop. Thus the connector is easily accessible and the catheter may easily be withdrawn from the container. Even more advantageously the longitudinal extent of the connector is furthermore larger than the longitudinal extent of the third section. Thus connector will extend partly out of the third section and will be even easier to grab hold of.

In a second aspect of the invention, which may be independent or combined with the first aspect described above the package comprises a container defining a compartment for containing a liquid and at least partly a medical device, said compartment extends in a longitudinal direction from a bottom of the container towards an opening of the container, and has an outer circumference of the container which decreases in at least a part of the longitudinal direction. Such decrease of the circumference may for example be obtained by shaping a part of the container in a conical shape, where the base of the cone is arranged at the bottom of the container. This allows the container to be more stable when placed in the vertical position. Furthermore it also allows the medical device to be easier pulled out of the container as the user may pull the medical device with one hand and use the other hand to grab around the container and brace against the decreasing circumference of the outer surface of the container.

FIGURES

Figure 2:
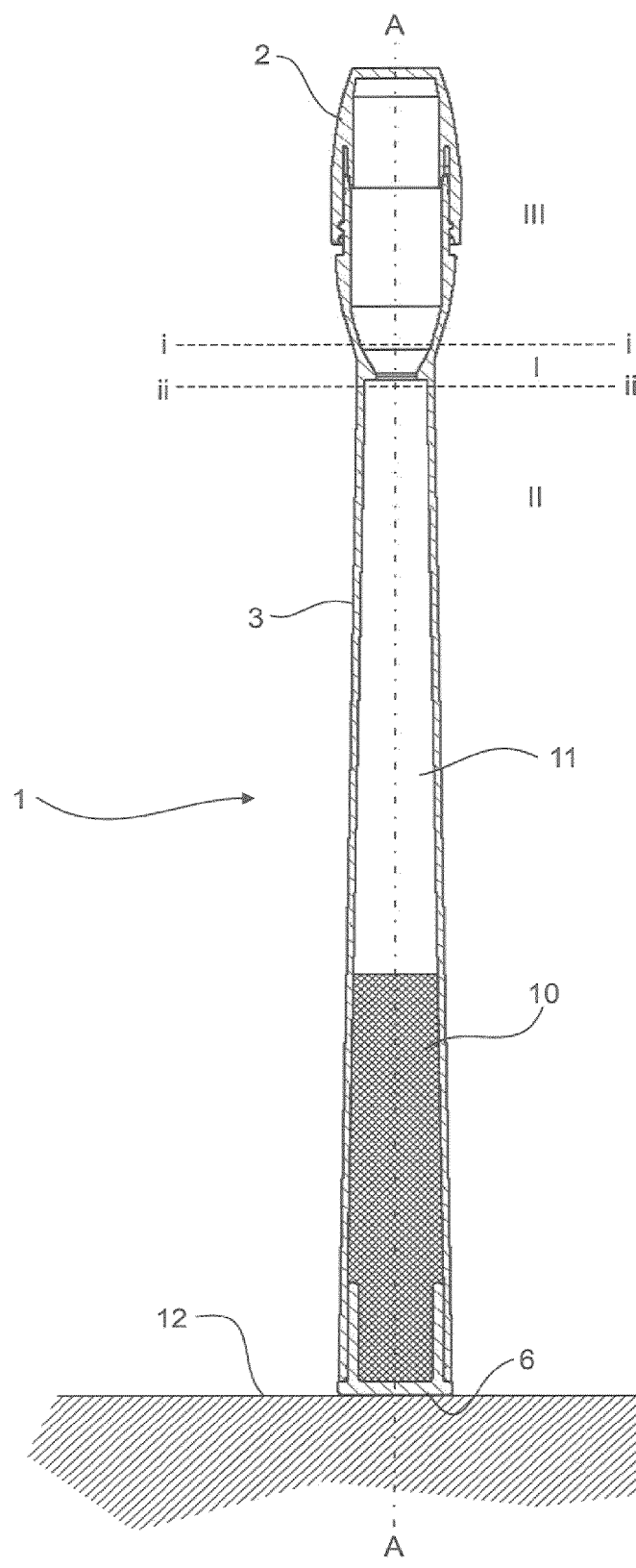
Figure 6:
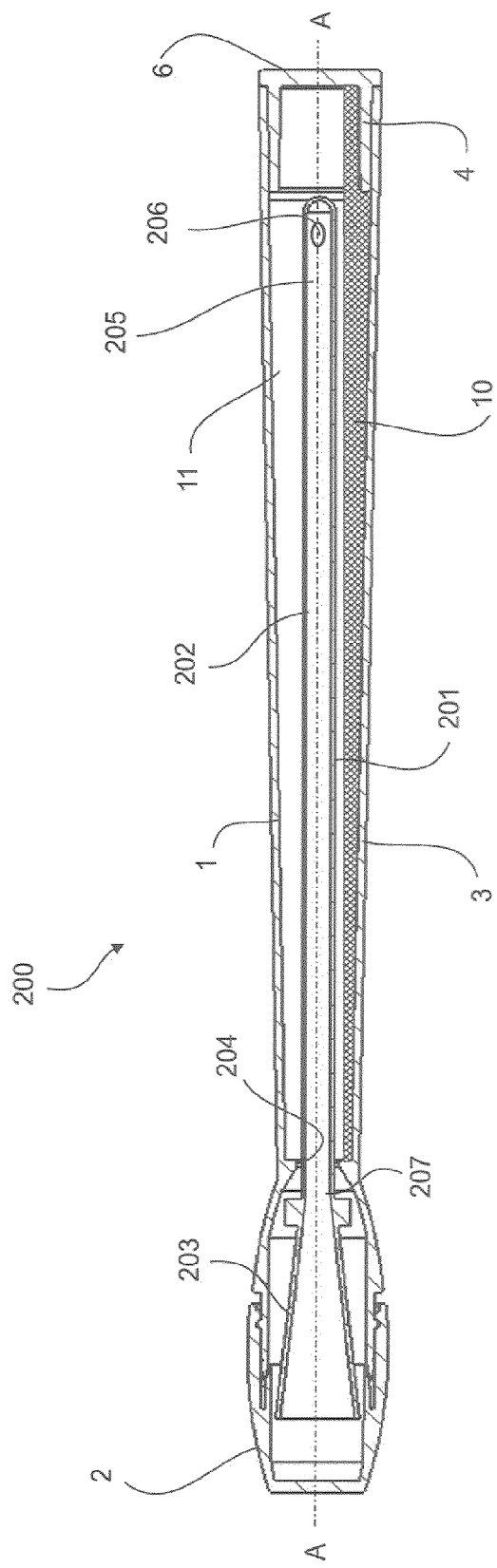

FIG. 1a shows in exploded view a container for use in a package according to the invention, FIG. 1b shows above container in an assembled configuration, FIG. 2 shows in a vertical position, and in section along line II-II in FIG. 1b, a container for use in a package according to the invention, FIG. 3a shows in a horizontal position, and in section along line II-II in FIG. 1b, a container for use in a package according to the invention, FIG. 3b shows the same as in FIG. 3a with indication of a sub-compartment according to one embodiment of the invention, FIG. 4 shows in a longitudinal sectional view another embodiment of a container for use in a package according to the invention, FIG. 5 shows the same embodiment in a cross-sectional view along the line V-V in FIG. 4, and FIG. 6 shows the embodiment of a container as shown in FIGS. 1-3b wherein a catheter has been arranged.

DETAILED DISCLOSURE

FIG. 1a shows in exploded view, and FIG. 1b shows in an assembled view, a container 1 used in a package according to the invention. The container consists of three injection-molded parts, a cap 2, a housing 3 and a plug 4. After production the plug 4 is fixed in the bottom end 5 of the housing 3, forming the bottom 6 of the container. Gluing, welding or any other method well known in the art for attaching components to each other can be used to fix the plug in the bottom end. Opposite the bottom end there is an opening 7. Thus, as seen in FIGS. 2, 3a and 3b, when the plug is fixed to the container, the opening, the housing and the plug define a compartment 11.

Close to the opening there is provided an outer thread 8 on the housing 3 formed to receive the inner thread 9 on the cap 2.

FIG. 2 shows the container placed in a vertical position where the bottom 6 is placed on a level or horizontal surface 12, such as a table or a bathroom sink. As can be seen, liquid 10, indicated by the hatched area, is contained in the compartment 11 of the container. FIGS. 3a and 3b shows the container placed in a horizontal position where the axis A-A is approximately parallel to the level or horizontal surface 12.

It should be understood, that in order to contain the liquid in the compartment the container provides a liquid tight closure. Thus, both the cap 2 and plug 4 is capable of engaging with the housing in a sealing manner.

In FIG. 3a dotted lines i-i and ii-ii are shown to approximately indicate first section I, placed between i-i and ii-ii; second section II, placed between ii-ii and the bottom 6 of the container; and third section III, placed between the opening 7 of the container and i-i.

As can be seen in FIG. 2 the second section II has an outer circumference, which increases towards the bottom 6. This creates a larger base for the container whereby it is more stable when placed in a vertical position on a leveled surface. Furthermore as the liquid seeks towards the bottom the stability of the container is further improved.

The cross-sectional area of the compartment in the first section I is smaller than the cross-sectional area of the compartment in the second section II. Furthermore, as the cross-sectional area of the container in the third section III is larger than the cross-sectional area of the container in the first section I, the first section I is raised in level and is thus more effective as a barrier against the liquid in the second section II. Thus, should the container accidentally tilt or otherwise be placed in its horizontal position as shown in FIG. 3a it is advantageously avoided that the liquid flows from the second section II, past the first section I and into the third section III. Thus, in case the cap is not in place when the container is in the horizontal position it is prevented that liquid spills out through the opening 7.

As can be seen from FIG. 3b the plane L and the circumference of the compartment between the inner shoulder 14 and the bottom of the compartment 15 define a sub-compartment 13. The plane L is a tangent plane to the circumference of the inner shoulder 14 and parallel to the longitudinal axis A-A of the compartment.

By providing, in the container, a volume of liquid 10 which is smaller than the volume of the sub-compartment, the liquid, as can be seen in FIGS. 3a and 3b will not spill over and out through the opening 7 in case the cap 2 is removed.

The container illustrated in FIGS. 1-3b is elongated and adapted for storing a catheter (not shown). Such a catheter is typically coated, and when stored together with a liquid it will be pre-wetted having hydrophilic properties and be ready for use as soon as the container is opened.

FIGS. 4 and 5 show a modified container 100, which is modified to prevent bending and kinking of especially a telescopic catheter when this is reinserted into the container after it has been used. In FIG. 4 the modified container is shown in a sectional view along its longitudinal direction and in FIG. 5 the modified container is shown in a cross sectional view along line V-V in FIG. 4 without the longitudinal section.

The modified container 100 has a housing 101 with a closed off end 102 and an outlet section 103. The outlet section has an outer thread 104 for coupling with a corresponding inner thread on a cap (not shown, but similar to cap illustrated in FIG. 1-3b) and the outlet section has an opening 105 through which a catheter may be pulled out of or inserted into the compartment 106 defined by the housing, the closed off end and the outlet section.

In the compartment there is provided a first, second, third and fourth support members 107a, 107b, 107c and 107d extending both in a longitudinal direction between the outlet section and the closed off end within the compartment and extending radially from the inner wall 108 of the compartment towards respective support surfaces 109a, 109b, 109c and 109d. As can be seen the supports member do not extend so far that they contact each other, this allows for first, second, third and fourth passages 110a, 110b, 110c and 110d to allow communication between a lumen 111, defined by the support surfaces and the passages, and first, second, third and fourth grooves 112a, 112b, 112c and 112d.

Thus when a catheter, as indicated by the broken circle 115 in FIG. 5, is inserted into the lumen the support surfaces will prevent the catheter from bending out to the sides in case a longitudinal force is applied which exceeds the bend or kink force of the catheter as described previously. Furthermore, in order to avoid that the catheter moves, bends or kinks into any of the grooves 112a, 112b, 112c and 112d the width of the passages, i.e. the shortest distance between each of the respective neighboring support surfaces, is smaller than the diameter of the catheter. In particular the width of the passages should be smaller than the diameter of the proximal section, i.e. the part of a telescopic catheter adapted to be inserted fully into the urethra, which is the section normally having higher flexibility than the distal section and thereby will bend or kink at the action of a lower longitudinal force.

By providing the grooves as illustrated the container is still capable of preventing the liquid from spilling out of the compartment in case the container is placed in its horizontal orientation. It can be understood, that the grooves are very much similar to the sub-compartment 13 as described with reference to FIG. 3b above. Thus, by providing a liquid in the compartment 106 which has a volume less than the volume of the individual grooves, the risk of spilling liquid when the container is placed in its horizontal orientation is further minimized.

Furthermore in order to prevent that the liquid flows on the support surfaces and out of the container first, second, third and fourth recesses (fourth recess not shown in the FIGS. 113a, 113b and 113c are provided between the support members and the first section formed as narrowing rim 114.

A package 200 according to the invention is shown in FIG. 6. The package consists of a container 1 seen in longitudinal section and as described in respect of FIGS. 1-3b above. In the compartment of the container there is provided a liquid 10 for and a hydrophilic-coated catheter 201. The catheter is formed of a catheter body 202 and a connector 203 attached to one end 204 (typically referred to the distal end) of the catheter body. At the other end 205 (typically referred to as the proximal end) of the catheter body there is provided an inlet opening 206 which allows for fluid communication between the inlet opening of the catheter body to outlet opening 207 provided at the distal end of the catheter body and out through the connector 203.

The connector 203 is formed as a hollow conical element. The connector has an axial length, which allows it to project out from the opening 7 of the container, while still being contained in the compartment when the container is closed. Thus, a user may easily grab the projecting part of the connector and pull the catheter out from the container.

The invention claimed is:

1. A catheter system comprising:
   a container including an outlet section providing a first outer diameter of the container and a first end of the container that defines an opening in the container, a bottom section providing a second outer diameter of the container and a sealed bottom wall at a second end of the container, and a third neck section providing a third outer diameter of the container that is located between the outlet section and the bottom section, the container further comprising:
   a tapered wall that converges from the second outer diameter to the third outer diameter such that the second outer diameter of the bottom section is larger than the third outer diameter of the neck section;
   wherein the first outer diameter of the outlet section is larger than the third outer diameter of the neck section;
   wherein the neck section has an inner shoulder providing an interior of the neck section with a cross sectional area that is smaller than an interior cross sectional area of either the outlet section or the bottom section; and
   a catheter that is disposed within the container, the catheter removable from the container for insertion into a bladder;
   wherein the inner shoulder of the neck section is configured to retain liquid between the neck section and the bottom section when the container is horizontal.

2. The catheter system of claim 1, further comprising:
   a cap attachable to the outlet section.

3. The catheter system of claim 2, wherein an exterior surface of the outlet section is threaded, and the cap is threaded and attachable to the outlet section.

4. The catheter system of claim 1, wherein a distal section of the catheter extends out of the outlet section of the container.

5. The catheter system of claim 1, wherein the interior of the neck section is configured to prevent liquid from flowing from the neck section into the outlet section when the container is horizontal.

6. The catheter system of claim 1, wherein the interior of the neck section defines a liquid compartment configured to receive and prevent liquid from flowing from the neck section into the outlet section when the container is horizontal.

7. The catheter system of claim 1, wherein the catheter is a telescoping catheter and a proximal section of the catheter is insertable into a bladder.

8. A catheter system comprising:
   a container including an outlet section providing a first outer diameter of the container and a first end of the container that defines an opening in the container, a bottom section providing a second outer diameter of the container and a sealed bottom wall at a second end of the container, and a third neck section providing a third outer diameter of the container that is located between the outlet section and the bottom section, the container further comprising:
   a tapered wall that converges from the second outer diameter to the third outer diameter such that the second outer diameter of the bottom section is larger than the third outer diameter of the neck section;
   wherein the first outer diameter of the outlet section is larger than the third outer diameter of the neck section;
   wherein the neck section has an inner shoulder providing an interior of the neck section with a cross sectional area that is smaller than an interior cross sectional area of either the outlet section or the bottom section;
   a catheter that is disposed within the container, the catheter provided as a telescoping catheter and having a proximal section that telescopes out of the container for insertion into a bladder; and
   means for preventing liquid from flowing from the neck section into the outlet section when the container is horizontal.

9. The catheter system of claim 8, wherein a distal section of the catheter extends out of the outlet section of the container.

10. The catheter system of claim 8, wherein the interior of the neck section is configured to prevent liquid from flowing from the neck section into the outlet section when the container is horizontal.

11. The catheter system of claim 8, wherein the interior of the neck section defines a liquid compartment configured to receive and prevent liquid from flowing from the neck section into the outlet section when the container is horizontal.

* * * * *